(12) United States Patent
Mouillet et al.

(10) Patent No.: US 9,155,627 B2
(45) Date of Patent: Oct. 13, 2015

(54) KNEE JOINT PROSTHESIS

(71) Applicant: Aesculap AG, Tuttlingen (DE)

(72) Inventors: Dominique Mouillet, Semoutiers-Montsaon (FR); Saïd Moussa, Chamarandes-Choignes (FR); Uwe Idler, Liptingen (DE)

(73) Assignee: AESCULAP AG, Tuttlingen (DE)

(*) Notice: Subject to any disclaimer, the term of this patent is extended or adjusted under 35 U.S.C. 154(b) by 236 days.

(21) Appl. No.: 13/832,355

(22) Filed: Mar. 15, 2013

(65) Prior Publication Data

US 2013/0204380 A1 Aug. 8, 2013

Related U.S. Application Data

(63) Continuation of application No. 13/251,337, filed on Oct. 3, 2011, now Pat. No. 8,491,661.

(30) Foreign Application Priority Data

Oct. 5, 2010 (EP) .................................. 10186622

(51) Int. Cl.
*A61F 2/38* (2006.01)
(52) U.S. Cl.
CPC .............. *A61F 2/3845* (2013.01); *A61F 2/3886* (2013.01); *A61F 2240/002* (2013.01)
(58) Field of Classification Search
CPC ................................. A61F 2/38; A61F 2/3868
USPC ........................................... 623/20.21, 20.27
See application file for complete search history.

(56) References Cited

U.S. PATENT DOCUMENTS

| | | | |
|---|---|---|---|
| 4,219,893 A | 9/1980 | Noiles | |
| 5,071,438 A | 12/1991 | Jones et al. | |
| 5,358,527 A | 10/1994 | Forte | |
| 5,395,401 A | 3/1995 | Bahler | |
| 5,755,801 A | 5/1998 | Walker et al. | |
| 5,782,925 A | 7/1998 | Collazo et al. | |
| 5,871,543 A | 2/1999 | Hofmann | |
| 5,871,545 A | 2/1999 | Goodfellow et al. | |
| 5,871,546 A | 2/1999 | Colleran et al. | |

(Continued)

FOREIGN PATENT DOCUMENTS

| | | |
|---|---|---|
| DE | 44 09 787 | 9/1995 |
| DE | 36 42 576 | 9/1996 |

(Continued)

*Primary Examiner* — Bruce E Snow
(74) *Attorney, Agent, or Firm* — Kenealy Vaidya LLP

(57) ABSTRACT

A knee joint endoprosthesis is provided which consists of a femur component and a tibia component having cooperating joint surfaces in contact with one another. A rotation guide arrangement is provided for forcing the femur component and the tibia component to rotate relative to each other about a medial center of rotation as a result of a flexure of the knee joint endoprosthesis. The rotation guide arrangement having a first guide element with a first guidance surface and a second guide element with a second guidance surface which cooperates with the first guidance surface. A projection of the tibia component comprises the first guide element and a transverse extension connecting condyles of the femur component comprises the second guide element. The first guidance surface defines a first radius of curvature and the second guidance surface defines a second radius of curvature. The first and second radii of curvature are identical.

24 Claims, 13 Drawing Sheets

(56) References Cited

U.S. PATENT DOCUMENTS

Figure 1A:
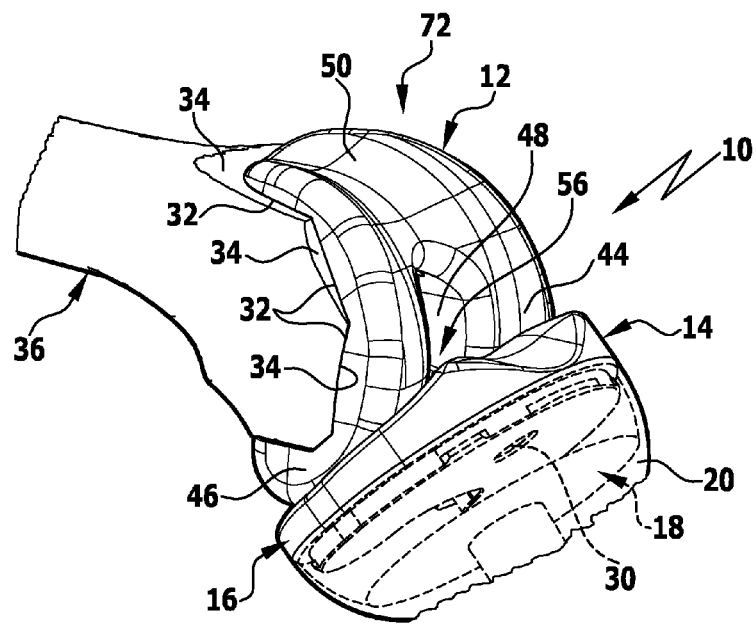

| | | |
|---|---|---|
| 5,879,392 A | 3/1999 | McMinn |
| 5,906,643 A | 5/1999 | Walker |
| 5,964,808 A | 10/1999 | Blaha et al. |
| 6,013,103 A | 1/2000 | Kaufman et al. |
| 6,056,779 A | 5/2000 | Noyer et al. |
| 6,080,195 A | 6/2000 | Colleran et al. |
| 6,165,223 A | 12/2000 | Metzger et al. |
| 6,210,445 B1 | 4/2001 | Zawadzki |
| 6,264,697 B1 | 7/2001 | Walker |
| 6,325,828 B1 | 12/2001 | Dennis et al. |
| 6,413,279 B1 | 7/2002 | Metzger et al. |
| 6,458,160 B2 | 10/2002 | Biegun et al. |
| 6,972,039 B2 | 12/2005 | Metzger et al. |
| 7,101,401 B2 | 9/2006 | Brack |
| 7,326,252 B2 * | 2/2008 | Otto et al. .................. 623/20.15 |
| 7,678,152 B2 | 3/2010 | Suguro et al. |
| 8,202,323 B2 | 6/2012 | Wyss et al. |
| 2001/0003803 A1 | 6/2001 | Leclercq |
| 2001/0018615 A1 | 8/2001 | Biegun et al. |
| 2003/0009232 A1 | 1/2003 | Metzger et al. |
| 2003/0153980 A1 | 8/2003 | Brack |
| 2004/0143339 A1 | 7/2004 | Axelson, Jr. et al. |
| 2004/0243244 A1 | 12/2004 | Otto et al. |
| 2005/0209701 A1 | 9/2005 | Suguro et al. |
| 2008/0097615 A1 | 4/2008 | Lipman et al. |
| 2008/0119940 A1 | 5/2008 | Otto et al. |
| 2009/0204221 A1 | 8/2009 | Walker |
| 2009/0326663 A1 | 12/2009 | Dun |
| 2009/0326666 A1 | 12/2009 | Wyss et al. |
| 2010/0016979 A1 | 1/2010 | Wyss et al. |
| 2010/0036499 A1 | 2/2010 | Pinskerova |
| 2010/0161067 A1 | 6/2010 | Saleh et al. |
| 2011/0040387 A1 | 2/2011 | Ries et al. |
| 2011/0130842 A1 | 6/2011 | Otto et al. |
| 2011/0184525 A1 | 7/2011 | Hagen |
| 2012/0203350 A1 | 8/2012 | Hagen et al. |

FOREIGN PATENT DOCUMENTS

| | | |
|---|---|---|
| DE | 695 03 381 | 4/1999 |
| DE | 100 12 060 | 10/2002 |
| DE | 697 25 291 | 7/2004 |
| DE | 697 34 268 | 5/2006 |
| DE | 600 23 953 | 8/2006 |
| DE | 102 00 263 | 1/2007 |
| DE | 20 2008 004 709 | 7/2008 |
| DE | 20 2009 012 704 | 12/2009 |
| DE | 20 2010 000 037 | 4/2010 |
| DE | 10 2008 017 394 | 5/2010 |
| EP | 0 519 873 | 12/1992 |
| EP | 0 634 156 | 5/1999 |
| EP | 1 127 560 | 8/2001 |
| EP | 1 378 216 | 1/2004 |
| EP | 1 095 637 | 12/2004 |
| EP | 1 591 082 | 11/2005 |
| EP | 0 927 009 | 1/2009 |
| EP | 2 145 606 | 1/2010 |
| FR | 2 707 871 | 1/1995 |
| GB | 2 184 025 | 6/1987 |
| WO | WO 98/46171 | 10/1998 |
| WO | 2007/119173 | 10/2007 |

* cited by examiner

FIG.3
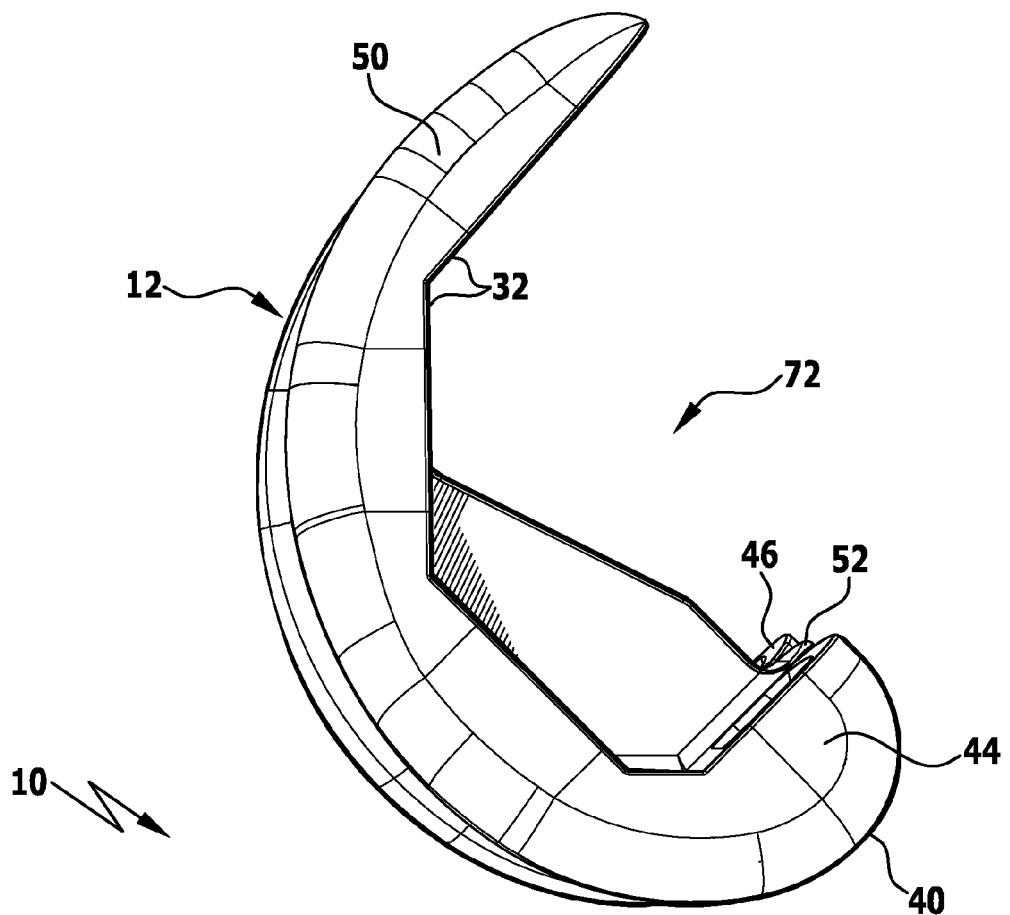
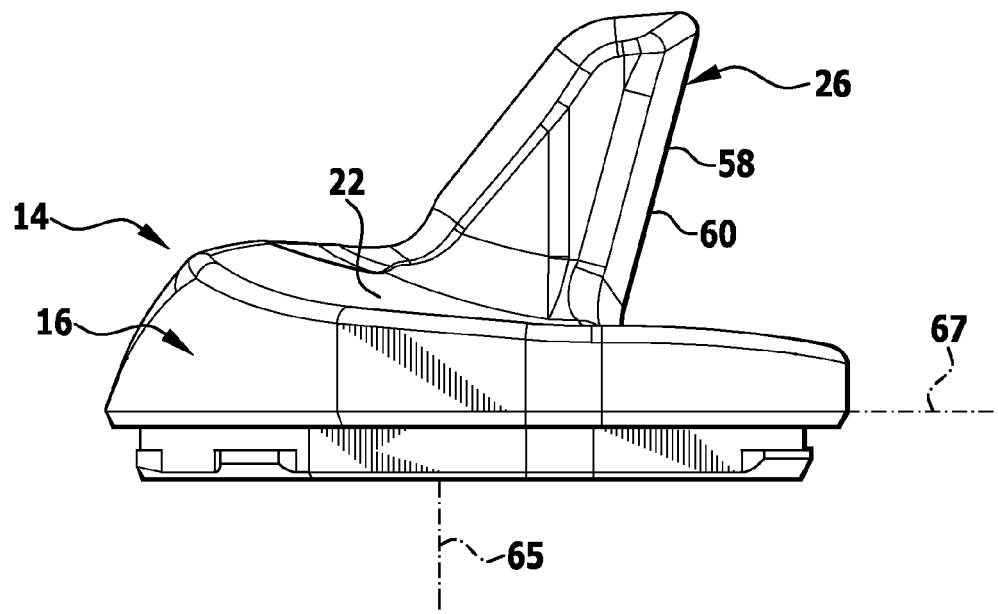

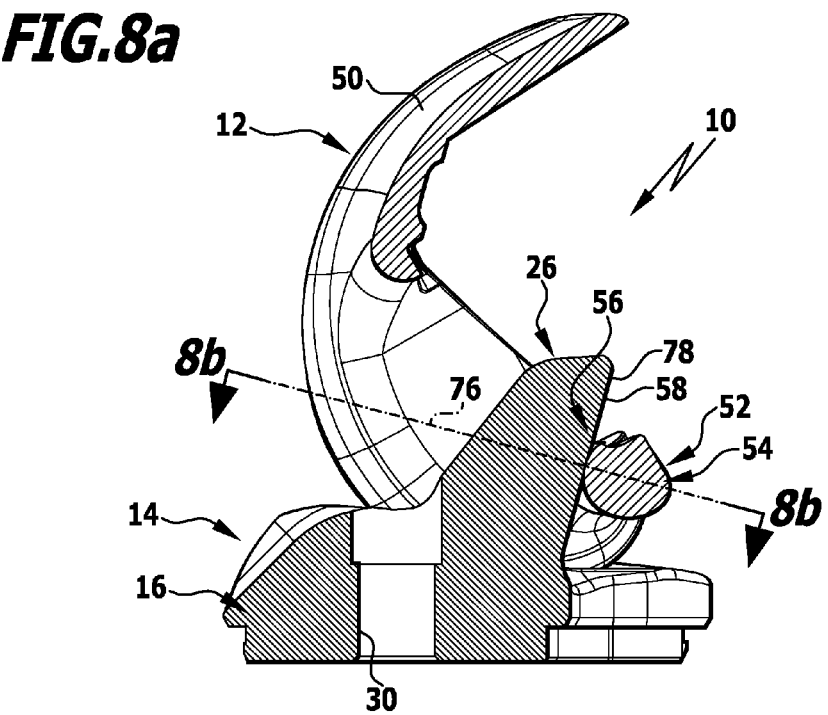
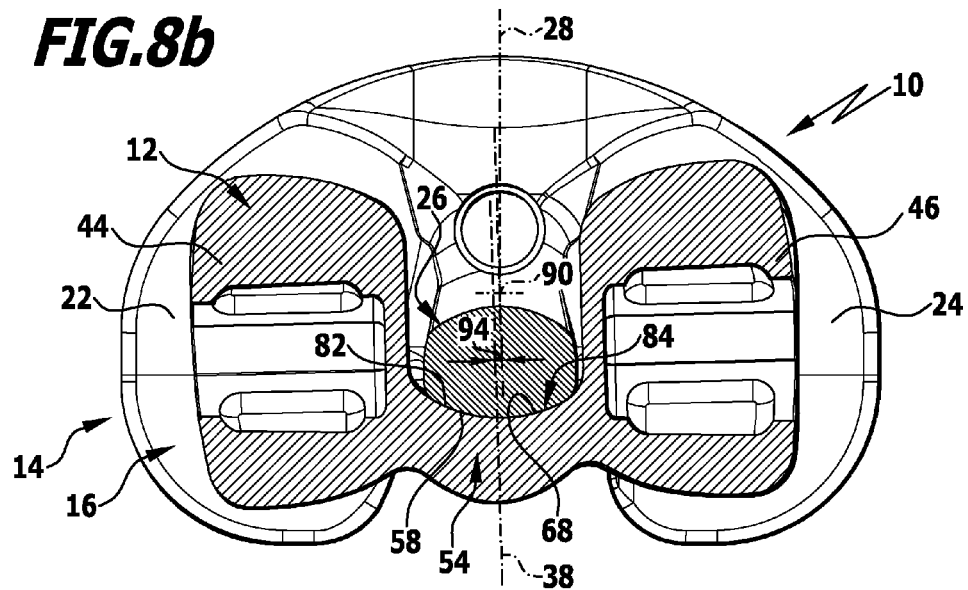

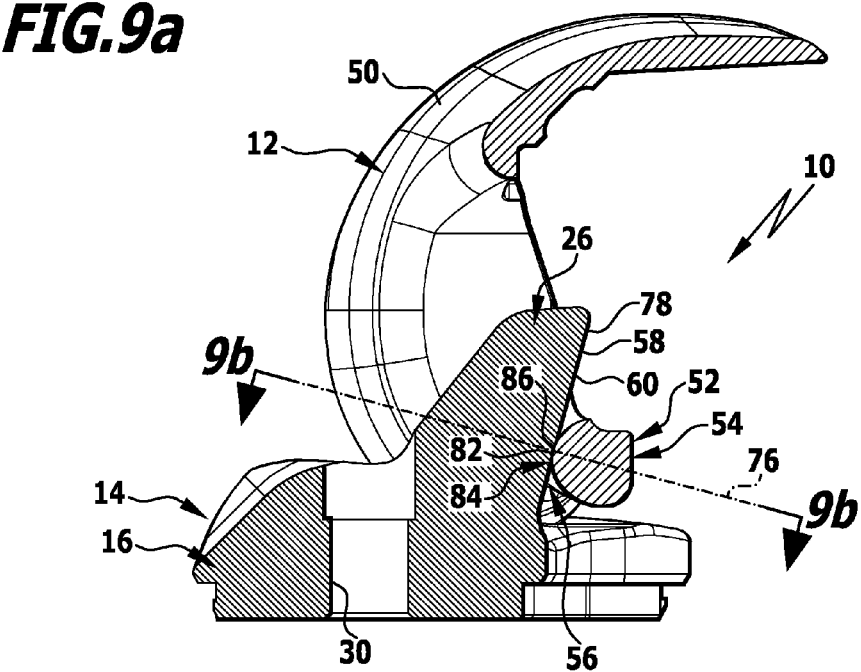
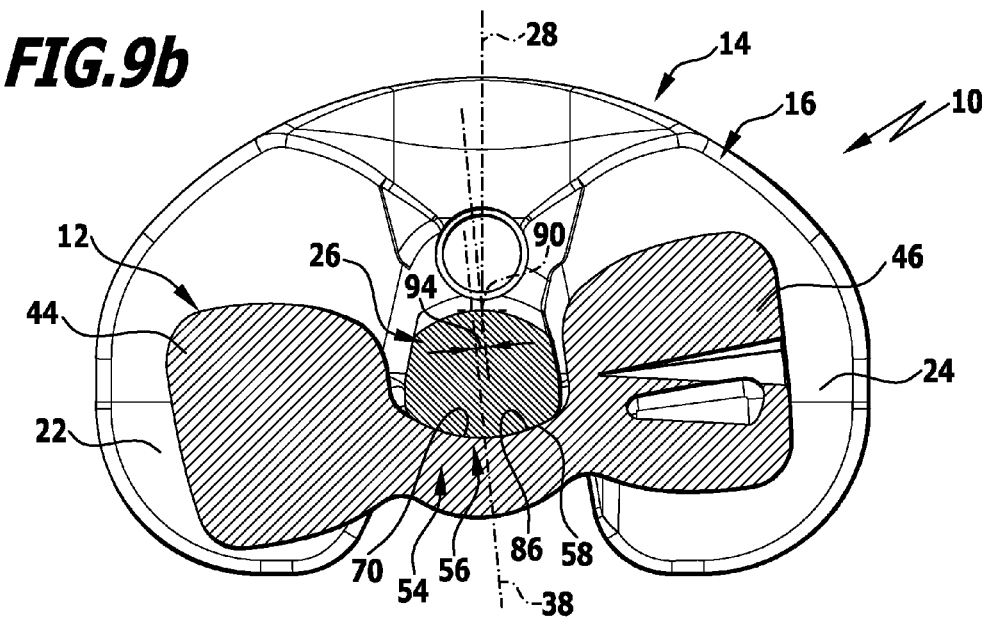

KNEE JOINT PROSTHESIS

CROSS-REFERENCE TO RELATED APPLICATIONS

This application is a continuation of commonly owned co-pending U.S. patent application Ser. No. 13/251,337, filed on Oct. 3, 2011, which claims the benefit of European Patent Application No. 10 186 622.6 filed Oct. 5, 2010, each of which are incorporated herein by reference in their entirety and for all purposes.

FIELD OF THE INVENTION

The present invention relates to knee joint endoprothesis generally, and more specifically to a knee joint endoprosthesis comprising a femur component and a tibia component which have cooperating joint surfaces that are in contact with one another, wherein furthermore, there is provided a rotation guide arrangement for forcing the femur component and the tibia component to rotate relative to each other about a medial center of rotation as a result of a flexure of the knee joint endoprosthesis.

BACKGROUND OF THE INVENTION

In recent years, importance has increasingly been attached to the best possible manner of imitating the natural kinematics of the knee when constructing knee joint endoprostheses. In a natural knee, the femur executes a rolling-sliding movement on the tibia. In the natural knee furthermore, there is superimposed on this so-called "roll-back" movement of the femur, a rotational movement about the longitudinal axis in the medial region of the knee, this also being referred to as the medial compartment. This medial rotational movement is also referred to as a "medial pivot" movement. This means that the medial part is almost stationary relative to the tibia during a walking cycle, i.e. a pivot point or a center of rotation is in essence defined on the medial side. On the other hand, the lateral part of the femur executes a sort of "banana-like" movement relative to the tibia in the dorsal direction. Thus, in toto, the overall kinematics of the natural knee joint during a normal walking cycle consist of a rotational movement of the femur about the medial joint surface of the tibia component.

A knee joint endoprosthesis having non-symmetrical joint surfaces of the tibia component is known from EP 0 927 009 A1 for example. However, in this knee joint endoprosthesis, the rotation guide arrangement is formed by the joint surfaces of the tibia component, namely, by the special shape thereof. On the other hand, a knee joint endoprosthesis of the type described hereinabove is known from EP 2 145 606 A1. The disadvantage of this known knee joint endoprosthesis however is that different femur and tibia components for the left knee and the right knee have to be provided for the right and left knee joint endoprostheses.

SUMMARY OF THE INVENTION

In accordance with the invention, a knee joint endoprosthesis comprises a femur component and a tibia component, which comprise cooperating joint surfaces that are in contact with one another. Furthermore, there is provided a rotation guide arrangement for forcing a rotational movement of the femur component and the tibia component relative to each other about a medial center of rotation due to a flexure of the knee joint endoprosthesis. The rotation guide arrangement comprises a first guide element having a first guidance surface and a second guide element having a second guidance surface which cooperates with the first guidance surface. The tibia component comprises the first guide element and the femur component comprises the second guide element. The first guidance surface defines a first radius of curvature and the second guidance surface defines a second radius of curvature. The first and second radii of curvature are identical.

BRIEF DESCRIPTION OF THE DRAWING FIGURES

Figure 1B:
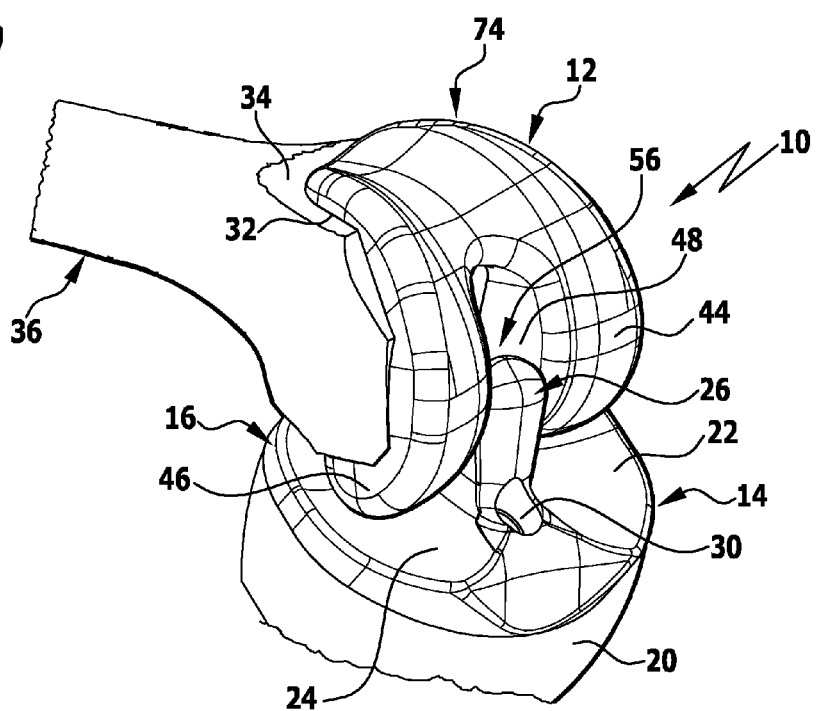
Figure 2:
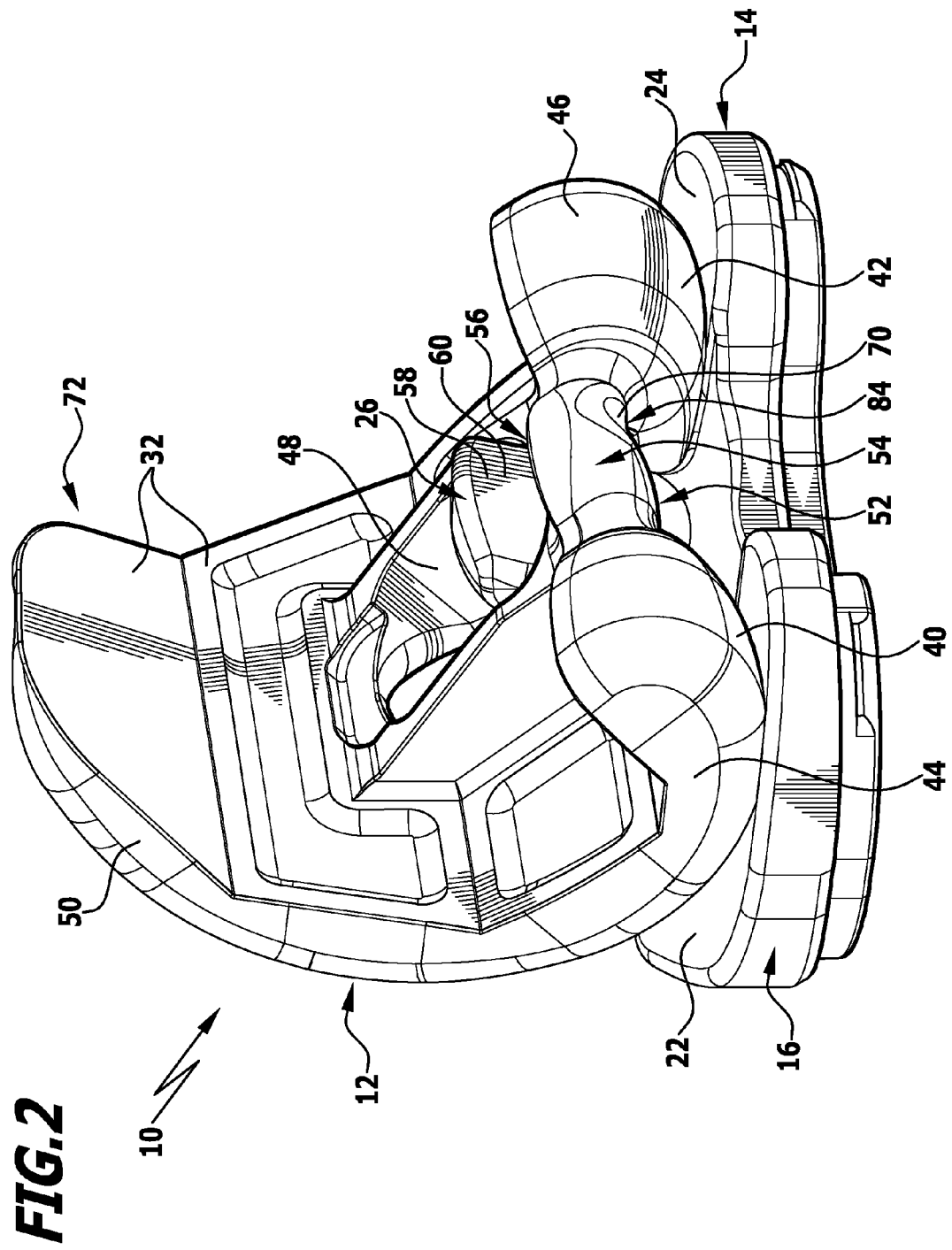
Figure 4:
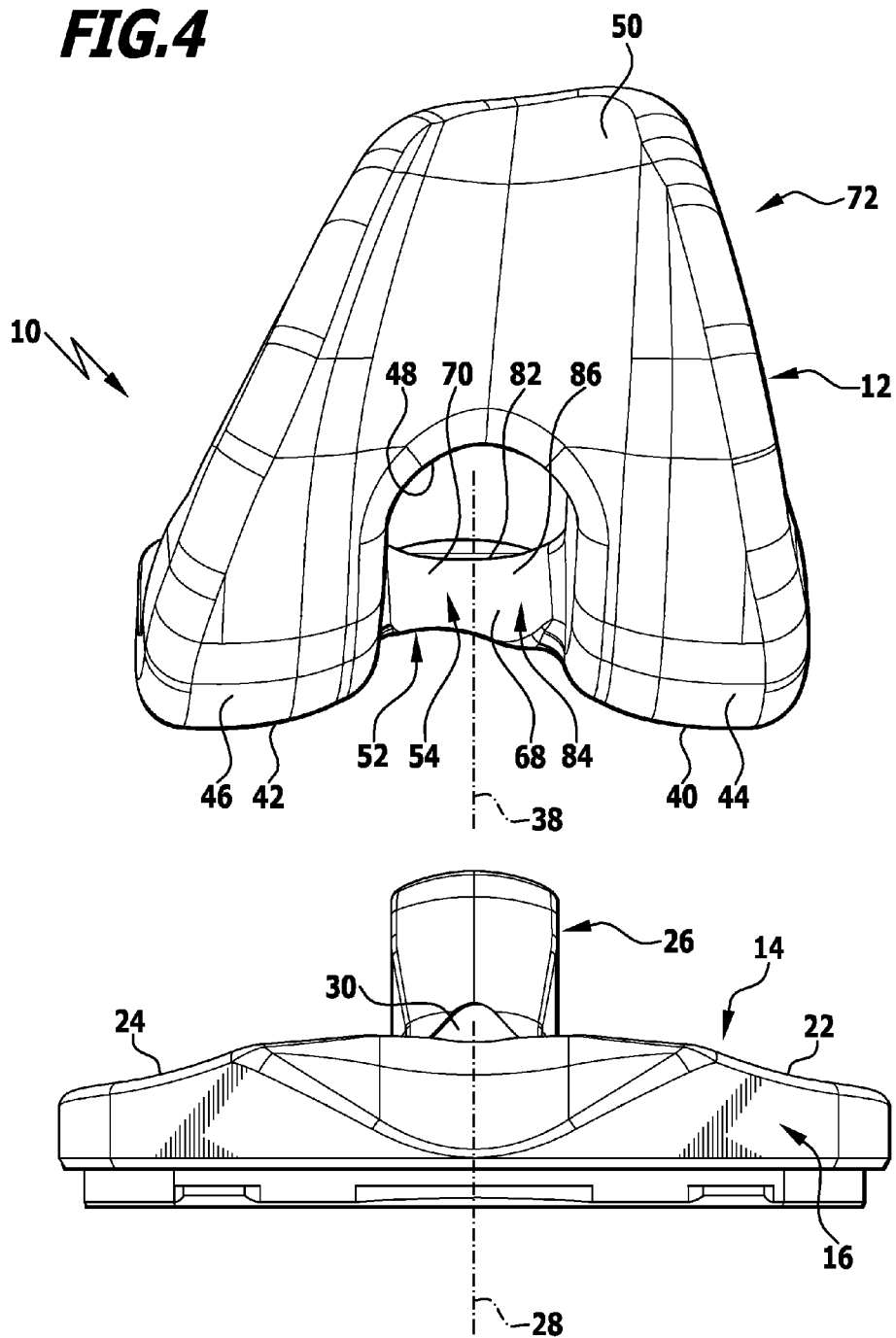
Figure 5:
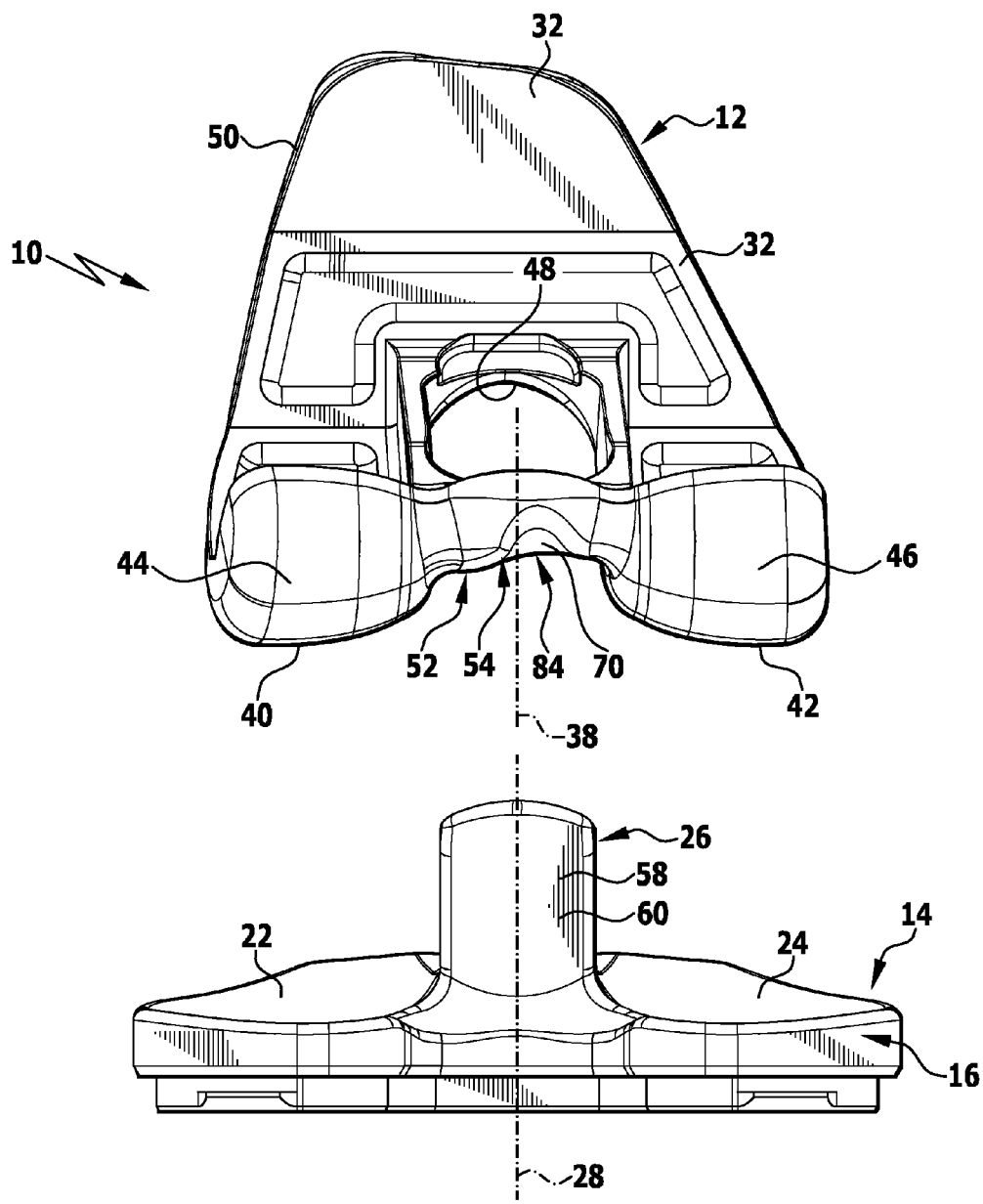
Figure 6A:
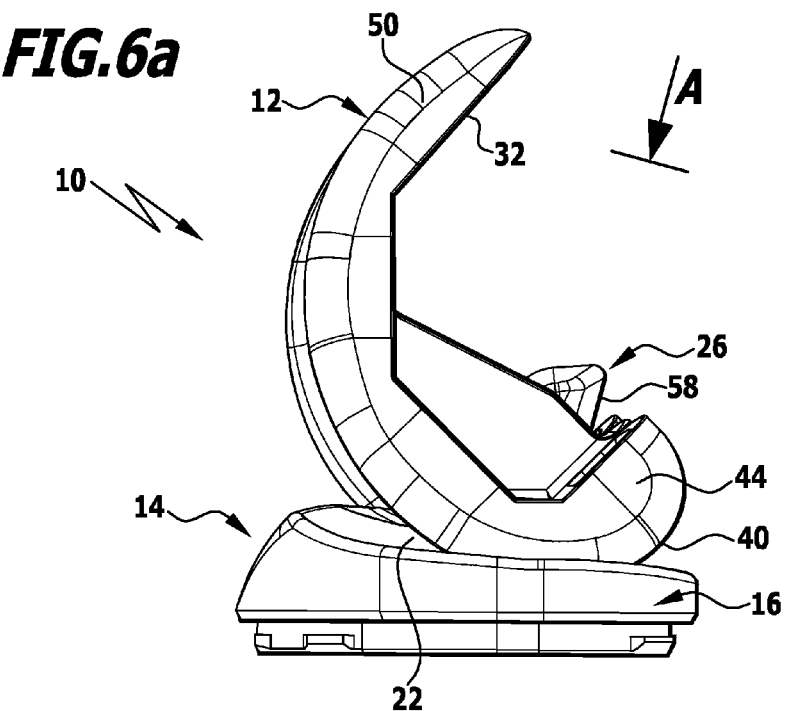
Figure 6B:
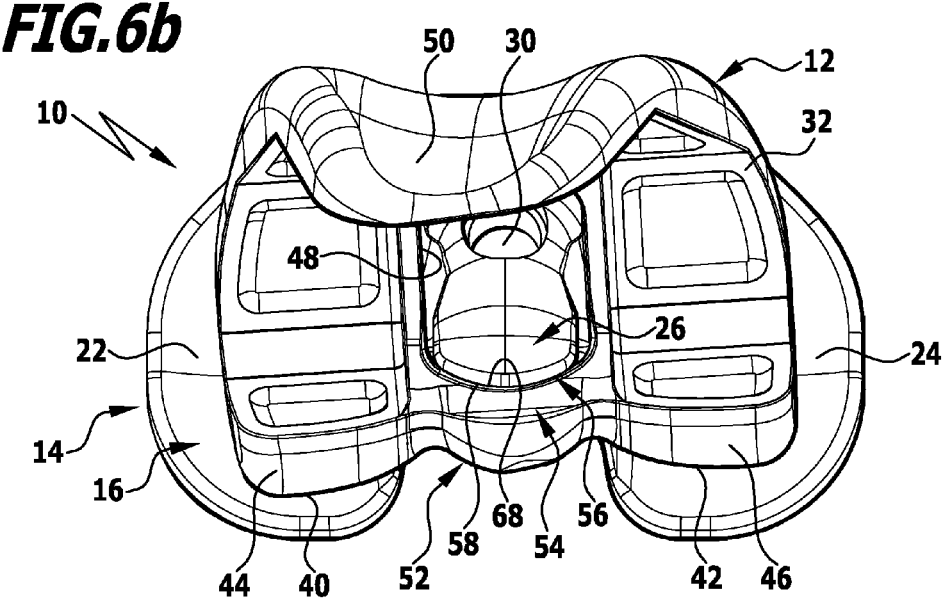
Figure 7A:
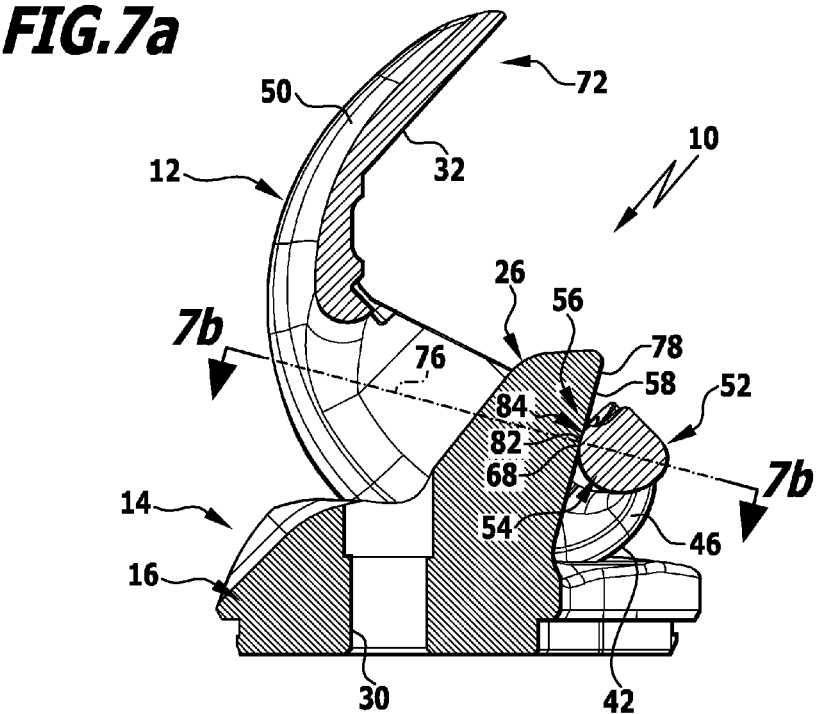
Figure 7B:
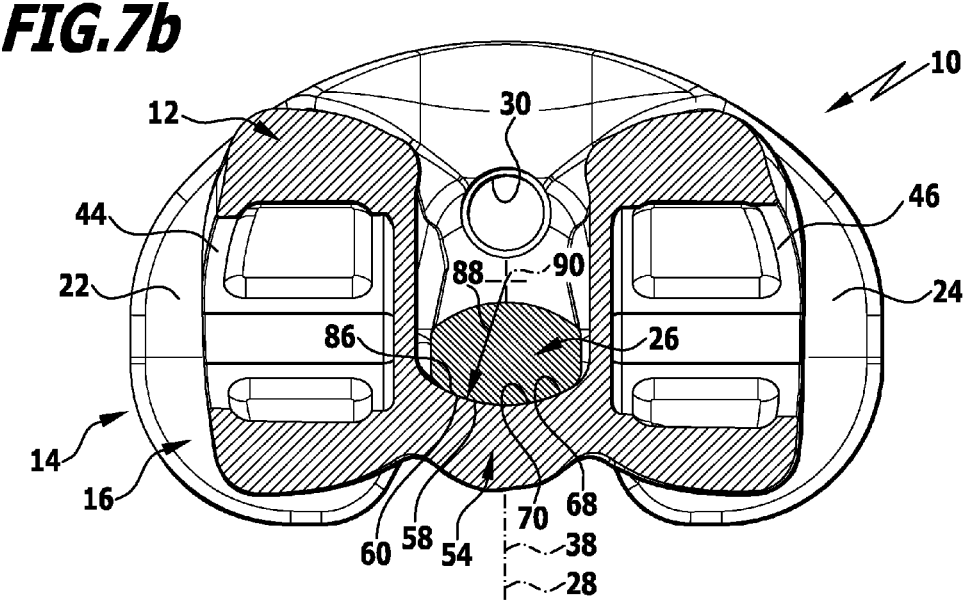
Figure 10A:
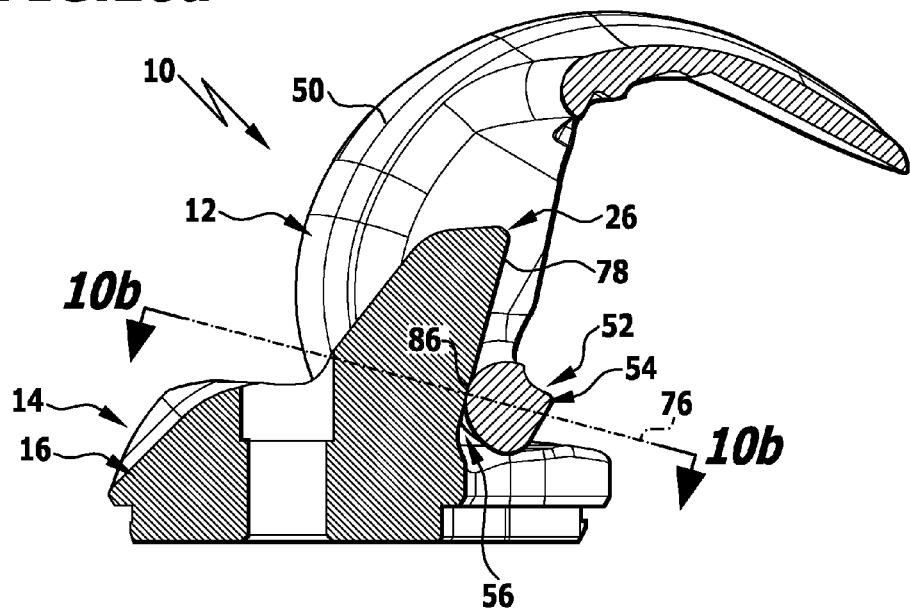
Figure 10B:
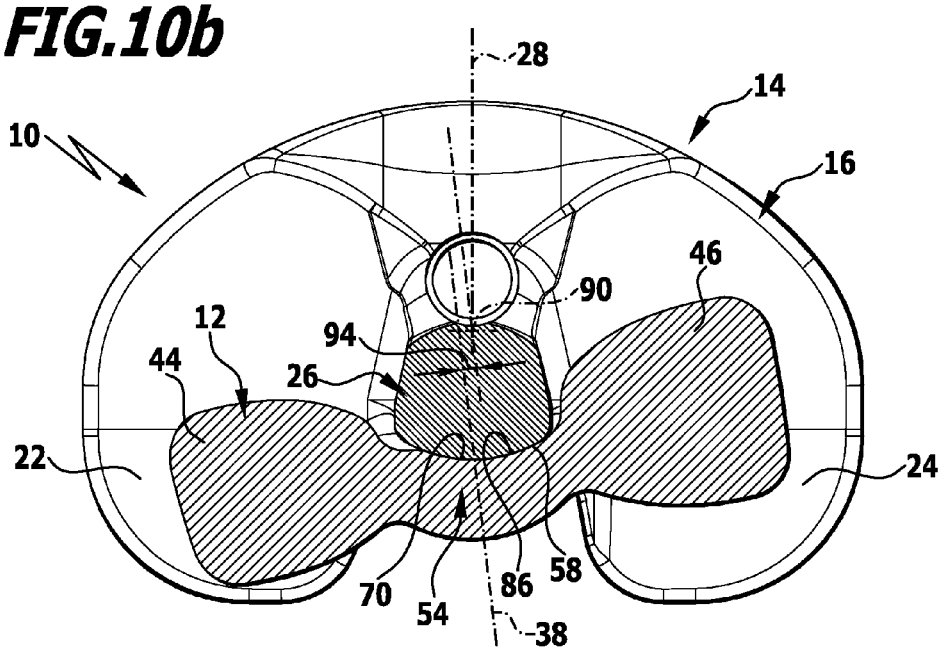
Figure 11A:
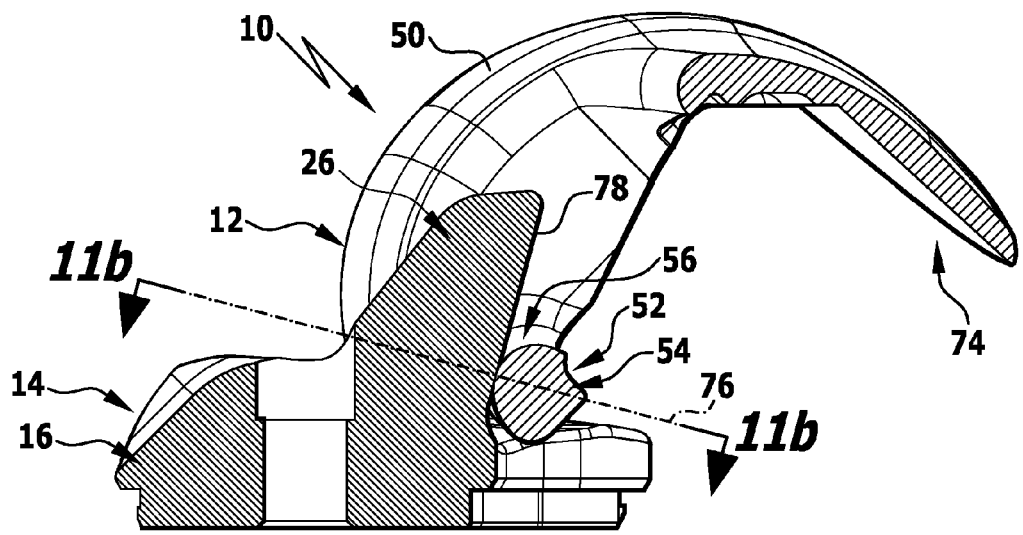
Figure 11B:
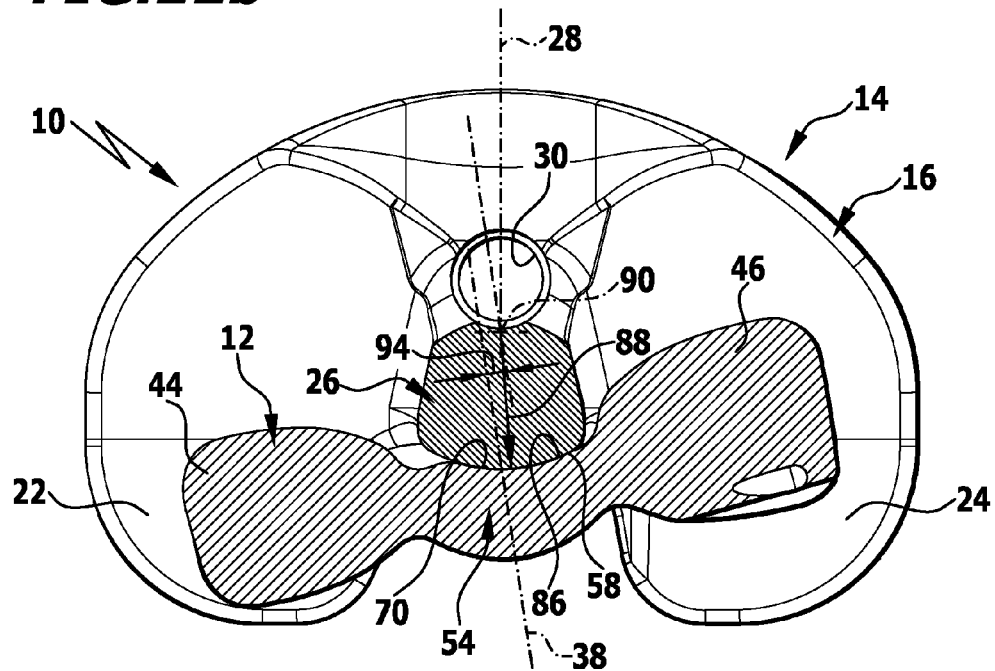
Figure 12:
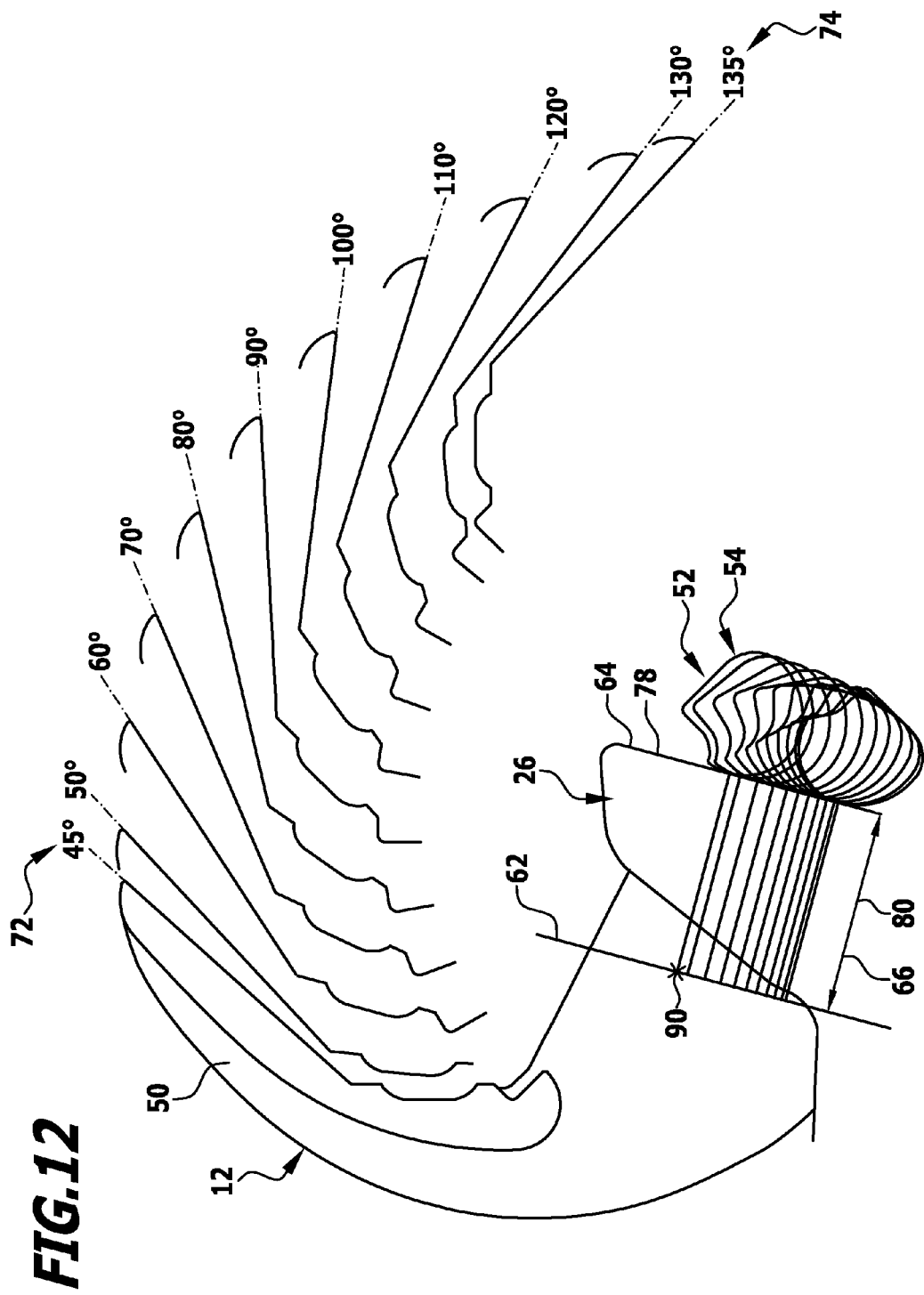
Figure 13:
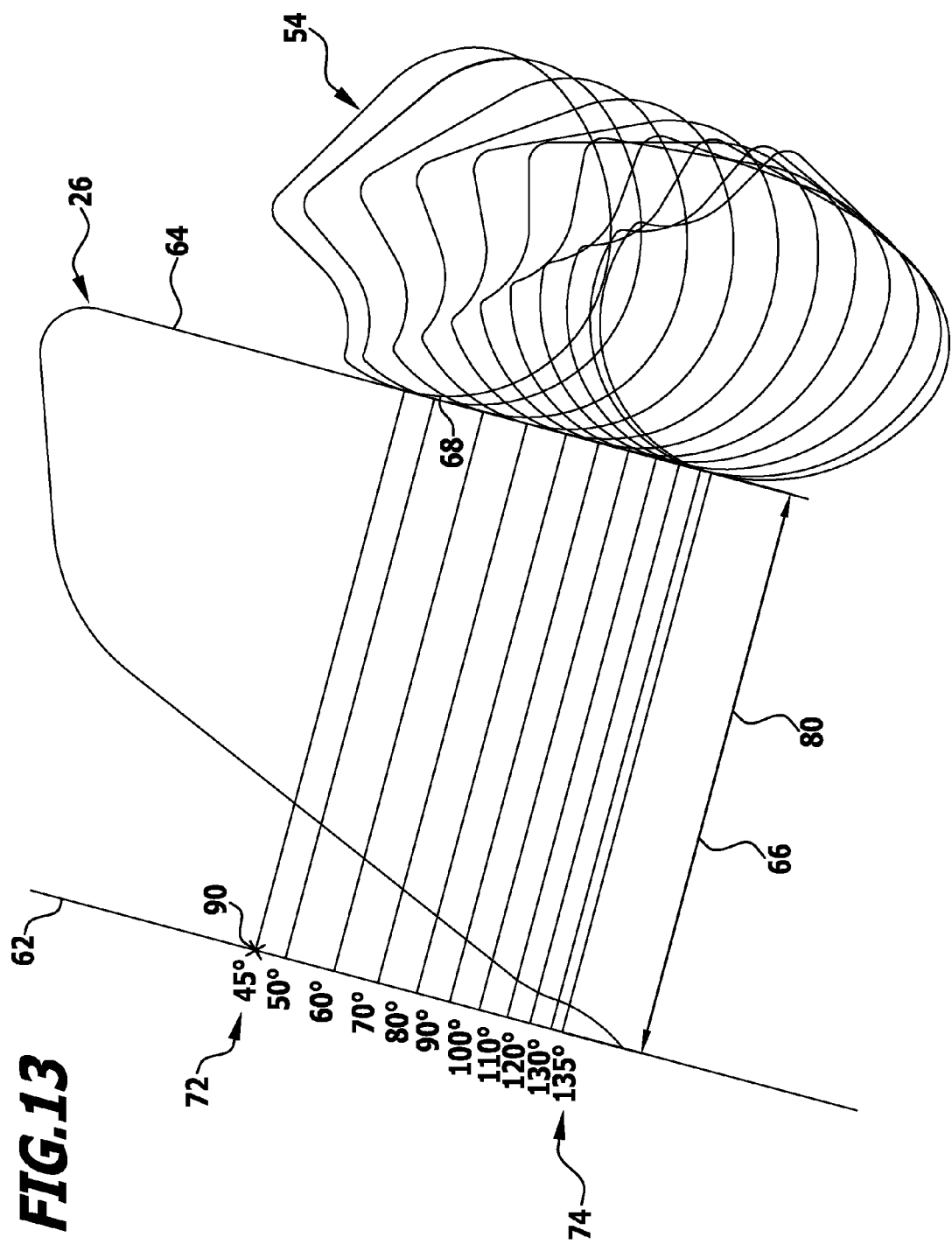

The foregoing summary and the following description may be better understood in conjunction with the drawing figures, of which:

FIG. 1a: shows a schematic perspective overall view of an implanted knee joint endoprosthesis which is slightly bent;

FIG. 1b: a schematic perspective overall view of a knee joint endoprosthesis depicted in FIG. 1 which is bent to a greater extent;

FIG. 2: a perspective overall view of the knee joint endoprosthesis depicted in Figure is in a bent position of approximately 45°;

FIG. 3: an exploded illustration of the knee joint endoprosthesis depicted in FIG. 2 in the form of a side view;

FIG. 4: a view of the knee joint endoprosthesis depicted in FIG. 3 from the front;

FIG. 5: a view of the knee joint endoprosthesis depicted in FIG. 3 from the rear;

FIG. 6a: a view of the knee joint endoprosthesis depicted in FIG. 2 from the side;

FIG. 6b: a plan view of the knee joint endoprosthesis depicted in FIG. 6a in the direction of the arrow A;

FIG. 7a: a sectional view of the knee joint endoprosthesis depicted in FIG. 6a in a bent position of approximately 45°;

FIG. 7b: a sectional view along the line 7b-7b in FIG. 7a;

FIG. 8a: a sectional view of the knee joint endoprosthesis depicted in FIG. 6a in a bent position of approximately 60°;

FIG. 8b: a sectional view along the line 8b-8b in FIG. 8a;

FIG. 9a: a sectional view of the knee joint endoprosthesis depicted in FIG. 6a in a bent position of approximately 90°;

FIG. 9b: a sectional view along the line 9b-9b in FIG. 9a;

FIG. 10a: a sectional view of the knee joint endoprosthesis depicted in FIG. 6a in a bent position of approximately 120°;

FIG. 10b: a sectional view along the line 10b-10b in FIG. 10a;

FIG. 11a: a sectional view of the knee joint endoprosthesis depicted in FIG. 6a in a bent position of approximately 135°;

FIG. 11b: a sectional view along the line 11b-11b in FIG. 11a;

FIG. 12: a schematic illustration of a bending movement of the knee joint endoprosthesis depicted in Figure is in an angular flexion range between 45° and 135°; and FIG. 13: an enlarged sectional view of the cooperating guide elements of a rotation guide arrangement of the knee joint endoprosthesis depicted in FIG. 12.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a knee joint endoprosthesis comprising a femur component and a tibia component, which comprise cooperating joint surfaces that are in contact with one another, wherein furthermore, there is provided a rotation guide arrangement for forcing a rotational movement of the femur component and the tibia component relative to each other about a medial center of rotation due to a flexure of the knee joint endoprosthesis, which rotation guide arrangement comprises a first guide element having a first guidance surface and a second guide element having a second guidance surface which cooperates with the first guidance surface, wherein the tibia component comprises the first guide element and the femur component comprises the second guide element, characterized in that the first guidance surface defines a first radius of curvature, in that the second guidance surface defines a second radius of curvature and wherein the first and second radii of curvature are identical.

A knee joint endoprosthesis constructed in such a manner enables the tibia component in particular to be formed such that it is completely mirror-symmetrical with respect to a mirror plane running in the anterior-posterior direction. Such a tibia component can then be used optionally for forming both an artificial left and an artificial right knee joint. In this way, the number of prosthesis components that one has to have ready can be significantly reduced. In particular, the number of prosthesis components that one has to have ready can then be reduced by half. Consequently, the stock-keeping costs for the manufacturer as well as those for the hospital in which the replacement of a totally or partly damaged knee joint by a knee joint endoprosthesis is effected can be significantly reduced. Moreover, mix ups in the implantation operation can also be prevented. Regrettably, these occur in practice time and time again since in the case of the numerous known knee joint endoprostheses, the differences between the right and the left tibia components are frequently not very great and are only discernable with difficulty by the operating surgeon. Despite the significantly simplified design of the knee joint endoprosthesis, it is well able to mimic the natural kinematics of the knee as described above. In particular, the rotation guide arrangement can at least partly take over the function of the rear cruciate ligament, i.e. it can additionally hold the femur component in position relative to the tibia component and also prevent slippage of the femur component relative to the tibia component in the anterior direction.

The design of the knee joint endoprosthesis can be simplified in particular if the first and the second radii of curvature are independent of the flexion angle of the knee joint endoprosthesis. In addition, the identical and constant radii of curvature of the two guidance surfaces make it possible for them to abut on one another in an optimal manner and thus, in comparison with known knee joint endoprostheses, there is significantly reduced surface pressure in the region where the guide elements of the rotation guide arrangement fit together.

The structure of the knee joint endoprosthesis is particularly simple, if the first guidance surface is formed such as to be mirror-symmetrical with respect to a first mirror plane running in the anterior-posterior direction. This special shaping of the first guidance surface makes it possible, in particular, for the tibia component as a whole, i.e. in its entirety, to be formed such that it is mirror-symmetrical with respect to the first mirror plane. In consequence, the tibia component can be used for the production of both a left and a right knee joint endoprosthesis.

The design of the knee joint endoprosthesis is particularly simple, if the first guidance surface defines a section of a cylinder surface. In other words, the first guide element can form a part of a cylinder, whereby the first guidance surface can form a part of an outer surface of the cylindrical region of the first guide element.

In accordance with a further preferred embodiment of the invention, provision may be made for the first and the second guidance surfaces to fit together along an even circular arc section within a flexion angle range which is defined by a minimum and a maximum flexion angle, and to roll upon one another and/or slide upon one another during a flexural movement. A knee joint endoprosthesis constructed in such a manner does not just enable the first and second guidance surfaces to touch one another in point-like manner as is frequently the case with known prostheses, but allows linear contact at least along the even circular arc section. In consequence, forces can be transferred between the femur and the tibia component in a significantly simpler and more positive manner. Then, for the same degree of stability, the size of the guide elements in particular could thus be made smaller in comparison with conventional knee joint endoprostheses. In particular, the knee joint endoprosthesis can be constructed in such a manner that the first and second guidance surfaces roll upon one another during a flexural movement of the knee. Alternatively however, they could also slide upon one another or undertake a combined sliding-rolling movement relative to each other.

The structure of the knee joint endoprosthesis can be simplified still further, if a radius of the circular arc section corresponds to the first and second radii of curvature. This can be achieved, in particular, if the second guide element acts perpendicularly on the first guidance surface.

Furthermore, it is expedient if the rotation guide arrangement defines a rotational axis for the rotational movement of the femur component and the tibia component relative to each other and if the rotational axis runs parallel to a line of intersection between the first guidance surface and the first mirror plane. The rotational axis that is defined in this way does not necessarily have to coincide with the medial rotational axis described above or the medial center of rotational movement between the femur and the tibia components. The defined rotational axis results because of the mutually corresponding construction of the first and second guidance surfaces. The superimposed rotational movement of the femur and tibia components about a medial center of rotation occurs as a result of the respective designs of the mating joint surfaces taking into consideration the superimposed sliding-rolling movement of the joint surfaces of the femur and tibia components that abut each another. In other words, the rotational axis described above is defined by the cooperating first and second guidance surfaces.

The structure of the knee joint endoprosthesis can be simplified still further if the circular arc section defines a plane of intersection which runs perpendicularly to the line of intersection. In addition thereby, it is ensured that the second guidance surface is always acts perpendicularly on the first guidance surface.

In principle, it would be conceivable for the line of intersection to be perpendicular or substantially perpendicular to a tibial plane defined by one of the tibia components. It is advantageous however, if the line of intersection is inclined relative to a surface-normal of a tibial plane defined by one of the tibia components. Preferably, a free end of the first guide element is inclined somewhat in the posterior direction. In this way, a movement of the femur component relative to the tibia component can be particularly well guided and in addition, luxation of the knee joint endoprosthesis is virtually prevented in a simple manner.

Furthermore, it is advantageous if the femur component comprises two joint surfaces which are constructed such as to be mirror-symmetrical with respect to a second mirror plane running substantially in the anterior-posterior direction. This makes it possible in particular for both the joint surfaces of the femur component and the joint surfaces of the tibia component to be constructed such as to be mutually mirror-symmetrical. Consequently, a certain asymmetry of the knee joint endoprosthesis is at best necessary for the second guidance surface and thus for the second guide element in order to construct a knee joint endoprosthesis having kinematics that are as natural as possible.

It can be expedient furthermore, if the second guidance surface is constructed in such a manner that a center point is defined for each flexion angle when there is a flexion of the knee joint endoprosthesis with a flexion angle within the flexion angle range of the circular arc section, and if the center points lie on a center point plane which runs parallel to the second mirror plane but offset in the lateral direction. By virtue of this special design of the second guidance surface, a transverse movement of the femur component relative to the tibia component somewhat in the medial direction can be preset in response to a bending movement of the knee.

Advantageously, the distance of the center point plane from the second mirror plane increases in dependence on the flexion angle. It is thereby possible in particular, for the femur component to rotate relative to the tibia component about a medial center of rotation in response to a flexural movement.

In principle, it would be conceivable for the spacing of the center point plane from the second mirror plane to increase linearly in dependence on the flexion angle. However, it is particularly expedient if a spacing of the center point plane from the second mirror plane increases nonlinearly in dependence on the flexion angle. A rotation guide arrangement incorporating such a dependency of the distance of the second mirror plane from the center point plane permits the kinematics of the natural knee to be reproduced almost to perfection.

Preferably, the two joint surfaces of the femur component are constructed in the form of condyle surfaces which are arranged such as to be mirror-symmetrical with respect to the second mirror plane. Such a femur component can be manufactured in a particularly simple and precise manner.

Expediently, the first mirror plane and the second mirror plane are identical in an extended position of the knee joint endoprosthesis. In other words, the first and the second mirror planes coincide when the knee is stretched, i.e. the bending or flexion angle between the femur and tibia components amounts to 0°.

In principle, it would be conceivable for the tibia component to be formed in one-piece. It is advantageous however, if the tibia component comprises a tibial part and a meniscus part that is mounted on the tibial part and if the meniscus part comprises joint surfaces which cooperate with the joint surfaces of the femur component. Such a construction of the tibia component consisting of at least two parts makes it possible, in particular, for the tibia component to be made of different materials. For example, the meniscus part could be made of a synthetic material having a high molecular weight such as polyethylene for example in order to produce joint surfaces having very good sliding properties. The tibial part could be made of a high-strength metallic material for example in order to achieve particularly high stability, in particular, for the anchorage thereof to the tibia. In particular thereby, the material may be a cobalt-chrome rootd alloy.

In principle, it would be conceivable to form the first guide element on the tibial part. However, the structure of the knee joint endoprosthesis can be simplified to a significant degree if the meniscus part comprises the first guide element. In particular, the first guide element can be constructed in the form of a protruding projection. Furthermore, the tibial part may, for example, comprise a tibial plate defining a tibial plane on which the meniscus part is seated over a large surface area. For example, it can be fixed there by means of a screw or another known connecting means in order to permit the meniscus part to be released from the tibial part in the case of a revision process.

It is advantageous, if the meniscus part and/or the tibial part are constructed such as to be mirror-symmetrical with respect to a first mirror plane running in the anterior-posterior direction. This means that the meniscus part or the tibial part can be selected to be mirror-symmetrical with respect to the first mirror plane. Optionally, both parts could also be constructed mirror-symmetrically. It is conceivable in particular, for the tibial part not to be mirror-symmetrical. This can be advantageous, in particular, if the tibial part is of modular construction in order to achieve individually optimised anchorage of the shaft of the tibial part on the remaining tibia of the patient for example.

It is expedient furthermore, if the second mirror plane and the first mirror plane are identical for flexion angles between the tibia component and the femur component which are smaller than a limiting angle. In other words, this means that the tibia and the femur can be bent relative to each other through an angular range commencing from a stretched position up to the defined limiting angle, whereby however, only bending occurs but there is still no rotational movement of the femur component relative to the tibia component about a medial center of rotation.

It is expedient, if the limiting angle corresponds to the minimum flexion angle of the flexion angle range. In particular, this enables the knee joint endoprosthesis to be constructed in such a manner that the first and the second guidance surfaces only make contact with one another starting from a flexion angle which corresponds to the limiting angle, but not on the other hand for smaller flexion angles.

Advantageously, the first radius of curvature has a value which lies in a range extending from approximately 7 mm up to approximately 15 mm. A first guidance surface having such a radius of curvature makes it possible to produce an adequately stable guide element be it the meniscus part or the tibial part.

In accordance with a preferred embodiment of the invention, the first radius of curvature amounts to 12 mm.

It is expedient, if the second guidance surface is defined by a section of an outer surface of a thread which has a rounded thread root having a thread-root radius which corresponds to the first radius of curvature. A design of this type for the second guidance surface makes it possible in particular to automatically force a transverse movement of the femur component relative to the tibia component as a result of a flexural movement. Such a transverse movement can be realized in a simple manner by means of the thread-like design of the second guidance surface. In particular, the size of a transverse movement can be deliberately set by the pitch of the thread for example. Furthermore, this design of the second guidance surface permits it to cooperate with a first, completely mirror-symmetrical first guidance surface and to realize a linear contact. Advantageously, the thread-root radius is independent of a rotary or rotational position of the second guide element, whereby the rotational position corresponds to the flexion angle of the knee.

It is particularly expedient, if the thread has a non-linear pitch. This enables a transverse movement to be realized in a form which is shared by such a movement of the natural knee Expediently, the pitch of the thread increases in dependence on the flexion angle. In this way, the rotation guide arrangement can force a relative movement between the femur component and the tibia component which emulates the natural knee in the best possible way.

Optimal conveyance of force from the first guide element to the second guide element and also vice versa can be achieved in particular if the second guide element is formed in a region between the joint surfaces of the femur component.

The function performed by the rear cruciate ligament can be taken over by the rotation guide arrangement in a particularly simple manner if the second guide element is formed in a posterior end region of the femur component.

It is expedient, if the femur component is constructed in one piece manner. The stability thereof can thereby be increased and the anchorage thereof on the remaining femur can also be simplified.

Furthermore, it can be advantageous for the tibial part and/or the meniscus part to be constructed in one piece manner. Here too, the stability of the respective parts can be improved by the one piece construction. However, it could also be advantageous for the tibial part to be in the form of a modularly constructed tibial part. It can then be adapted individually to the physiology of the patient in order to achieve optimal anchorage on the remaining tibia.

It is expedient, if the tibia component is constructed in one piece manner. In particular, this enables the tibial part and the meniscus part to be constructed together in one piece manner. Furthermore, this arrangement opens up the possibility of making the tibia component completely out of a synthetic material. For example, polyethylene, preferably polyethylene of high molecular weight (HMW-PE) can be selected as the material for such a one piece tibia component.

An exemplary embodiment of a knee joint endoprosthesis which bears the general reference symbol 10 and is illustrated schematically in the Figures comprises a femur component 12 and a tibia component 14. In turn, the tibia component 14 comprises a meniscus part 16 that is constructed in one piece manner as well as a tibial part 18 which is illustrated schematically in FIG. 1 by means of the dashed lines and is arranged to be anchored in a partially resected tibia 20 of a patient. The tibial part 18 can be constructed in one-piece or multi-piece manner, whereby, for the purposes of producing a modular tibial part 18, several parts, i.e. at least two, can typically be provided, in particular, with shafts of different lengths.

The meniscus part 16 comprises a medial joint surface 22 and a lateral joint surface 24 which are formed on an upper surface of the meniscus part 16. Between the joint surfaces 22 and 24, there is formed a first guide element 26 which protrudes from the upper surface of the meniscus part in the form of a projection. The meniscus part 16 is constructed such as to be fully mirror-symmetrical with respect to a first mirror plane 28 which runs in the anterior-posterior direction. For the purposes of fixing the meniscus part 16 to the tibial part 18, there serves a not illustrated screw which passes through a boring 30 formed symmetrically in the meniscus part 16. The boring 30 is widened in stepped manner in the direction of the femur component 12 so as to accommodate the head of the screw. The boring 30 is arranged to adjoin the first guide element 26 in the anterior direction and it represents a connection between the upper and the lower surface of the meniscus part 16.

The femur component 12 comprises a bone contact surface 32 having several surface sections which are arranged to be placed on corresponding, prepared cut surfaces 34 of a prepared femur 36 and are fixable thereto especially by means of bone cement. The surface sections are preferably flat at least in part and are provided with recesses for the bone cement.

Two joint surfaces which are mirror-symmetrical with respect to a second mirror plane 38 and face in the direction of the tibia component 14 are provided on the femur component 12, namely, a medial joint surface 40 and a lateral joint surface 42 which define a medial condyle 44 on the one hand and a lateral condyle 46 on the other. The two condyles 44 and 46 are separated from one another by a recess 48 and are connected together in an anterior end region 50. The condyles 44 and 46 are connected together by a second guide element 54 in a posterior end region 52. The second guide element 54 extends substantially transversely with respect to the second mirror plane 38. It is not mirror-symmetrical with respect to the second mirror plane 38 as will be explained in detail in the following.

The medial joint surfaces 22 and 40 and also the lateral joint surfaces 24 and 42 are constructed as mutually corresponding pairs in order to allow a superimposed sliding-rolling movement between the femur and the tibia component 12, 14.

The first guide element 26 and the second guide element 54 each form a part of a rotation guide arrangement bearing the general reference symbol 56. The first guide element 26 comprises a first guidance surface 58 which is likewise mirror-symmetrical with respect to the first mirror plane 28. It forms a section of an outer cylinder surface 60. A center point line 62 of the cylinder surface 60 runs parallel to a line of intersection 64 between the first guidance surface 58 and the first mirror plane 28. The line of intersection 64 is inclined relative to a surface-normal 65 of a tibial plane 67 defined by the tibia component 14. A first radius of curvature 66 of the cylinder surface 60 is thus defined by the distance of the center point line 62 and the line of intersection 64 from each other. The first radius of curvature 66 preferably lies in a range of from approximately 7 mm up to approximately 15 mm and amounts to 12 mm in the case of the exemplary embodiment illustrated schematically in the Figures.

The second guide element 54 defines a second guidance surface 68 which fits the first guidance surface 58 along a flat circular arc section 70 within a flexion angle range defined by a minimum and a maximum flexion angle. The first and second guidance surfaces 58, 68, in dependence on the arrangement, roll upon one another and/or slide upon one another as the result of a flexural movement. They preferably roll away from one another. A minimum flexion angle 72 amounts to approximately 45° in the exemplary embodiment illustrated in the Figures, a maximum flexion angle 74 amounts to 165° in the exemplary embodiment illustrated in the Figures. Consequently, a flexion angle range of from approximately 45° to approximately 165° is defined. Optionally a minimum flexion angle can lie in a range of approximately 20° to approximately 60°, a maximum flexion angle within a range of approximately 120° to approximately 190°.

The respective flexion angle is determined between a stretched position in which the femur and the tibia substantially define a common longitudinal axis, and a corresponding bent position between the femur and the tibia. Each circular arc section 70 thus defines a contact line between the first guidance surface 58 and the second guidance surface 68 in each bent position. Furthermore, each circular arc section 70 defines a respective plane of intersection 76 which runs perpendicularly to the line of intersection 64. The line of intersection 64 thus forms a surface-normal 78 to all possible planes of intersection 76. In each plane of intersection 76, the second guidance surface 68 thus defines a second radius of curvature 80 which corresponds to the first radius of curvature 66.

The first and the second radii of curvature 66, 80 are independent of a flexion angle of the knee joint endoprosthesis 10 and remain constant in each case. This is achieved by means of the cylinder surface 60 in conjunction with the specially designed second guidance surface 68. This is defined by a section of an outer surface 82 of a thread 84 or a similar screw-shaped body. The thread 84 has a rounded thread root 86 having a thread-root radius 88 which corresponds to the first radius of curvature 66 as well as to the second radius of curvature 80. Alternatively, one could also say that the second guidance surface 68 defines a part of an outer screw surface. The special feature of the second guidance surface 68 is that the thread-root radius 68 does not change, namely, independently of the flexion position of the femur component 12 and the tibia component 14 relative to each other. Consequently, they always abut one another along a flat circular arc section 70 as is illustrated in FIGS. 7a to 11b and as is easily perceptible therein.

It should be mentioned, that the first guidance surface 58 and the second guidance surface 68 are not in contact with one another for flexion angles smaller than approximately 45°, i.e. for flexion angles which are smaller than the minimum flexion angle 72. The minimum flexion angle thus forms a limiting angle.

Due to the identical radii of curvature 66 and 80 of the first and second guidance surfaces 58 and 68, the center points 90 of the circular arc sections 70 all lie on the center point line 62 which defines a straight line.

As schematically illustrated in FIGS. 12 and 13, the second guide element 54 migrates in the direction of the meniscus part 16 when the knee flexes with an increasing flexion angle. In the case of this rolling and/or sliding movement, which is preferably a pure rolling movement of the first and second guide elements 26 and 54 relative to each other, the second mirror plane 38 is simultaneously displaced somewhat in the medial direction taken with reference to a center point plane 92 containing all the center points 90. A spacing 94 between the second mirror plane 38 and the center point plane 92 increases nonlinearly in dependence on the flexion angle. For flexion angles below the minimum flexion angle 72, the spacing 94 amounts to zero, for a flexion angle of 90° it is about 1.4 mm and for a flexion angle of 120° it is about 2.0 mm.

This displacement in the transverse direction is achieved by the screw-shaped design of the second guidance surface 68 which causes a transverse movement as a result of a flexural movement. This rotational movement and lateral movement of the femur component 12 relative to the tibia component 14 is easily perceptible in FIGS. 7b to 11b. The center point plane 92 in each case cuts the first mirror plane 28 at a center point 90, as is evident from the sectional views illustrated in FIGS. 7b to 11b. Since, by definition, the center point plane 92 runs parallel to the second mirror plane 38, but the center of rotational movement defined by the rotation guide arrangement 56 is through the center point line 62, there thus results a displacement of the femur component 12 and thus of the second mirror plane 38 as a result of a bending of the knee in the medial direction.

Thus, if one regards the overall system consisting of the femur component 12 and the tibia component, the center points 90 in the appertaining planes of intersection 76 are congruent in each case, as inevitably arises as a result of the identical first and second radii of curvature 66 and 80. Consequently, the respective center point 90 in one of the planes of intersection 76 is always on the line of intersection between the center point plane 92 and the first mirror plane 28, namely, independently of the respective flexion angle.

During the rolling movement, i.e. during a walking cycle with increasing flexion angle, the second guide element 54 rolls on the first guide element 26 and, as already stated, simultaneously executes a downward movement on the first guide element 26 as well as a rotational movement about the center point line 62. The pivot point of the femur component 12 is thereby in the common center point 90 of the first and second guidance surfaces 58 and 68 and thus on the center point line 62. The rotational movement caused by the eccentricity of the center point 90 of the second guidance surface 68, namely, due to its different location in different but mutually parallel planes of intersection 76, leads to the fact that the knee joint endoprosthesis 10 imitates the desired and initially described "medial pivot" kinematics as bending increases. Due to the position of the pivot point, the kinematics which the previously described knee joint endoprosthesis 10 executes, is not however a purely "medial pivot" characteristic. This means that the medial joint surface 22 and the medial joint surface 40 do not always touch each other at the same point of contact which ideally is independent of a bending angle. Furthermore, the femur component 12 executes a rotational movement which is somewhat greater on the lateral side than on the medial side.

What is claimed is:

1. A knee joint endoprosthesis, comprising:
   a femur component and a tibia component, which comprise cooperating joint surfaces that are in contact with one another,
   a rotation guide arrangement for forcing a rotational movement of the femur component and the tibia component relative to each other about a medial center of rotation due to a flexural movement of the knee joint endoprosthesis, which rotation guide arrangement comprises a first guide element having a first guidance surface and a second guide element having a second guidance surface which cooperates with the first guidance surface,
   wherein:
      a projection of the tibia component comprises the first guide element,
      a transverse extension connecting condyles of the femur component comprises the second guide element,
      the first guidance surface defines a first radius of curvature,
      the second guidance surface defines a second radius of curvature,
      the first and second radii of curvature are identical,
      the second guidance surface is defined by a section of an outer surface of a thread which has a rounded thread root having a thread-root radius which corresponds to the first radius of curvature,
      a pitch of the thread establishes an extent of a forced transverse movement of the femur component relative to the tibia component during the flexural movement.

2. A knee joint endoprosthesis in accordance with claim 1, wherein the first and the second radii of curvature are independent of a flexion angle of the knee joint endoprosthesis.

3. A knee joint endoprosthesis in accordance with claim 1, wherein the first guidance surface is mirror-symmetrical with respect to a first mirror plane running in an anterior-posterior direction.

4. A knee joint endoprosthesis in accordance with claim 1, wherein the first guidance surface defines a section of a cylinder surface.

5. A knee joint endoprosthesis in accordance with claim 1, wherein the first and the second guidance surfaces abut against each other along an even circular arc section within a flexion angle range which is defined by a minimum and a maximum flexion angle, and at least one of roll upon one another and slide upon one another during the flexural movement.

6. A knee joint endoprosthesis in accordance with claim 5, wherein a radius of the circular arc section corresponds to the first and second radii of curvature.

7. A knee joint endoprosthesis in accordance with claim 3, wherein:
the rotation guide arrangement defines a rotational axis for the rotational movement of the femur component and the tibia component relative to each other, and
the rotational axis runs parallel to a line of intersection between the first guidance surface and the first mirror plane.

8. A knee joint endoprosthesis in accordance with claim 5, wherein:
the first guidance surface is mirror-symmetrical with respect to a first mirror plane running in an anterior-posterior direction, and
the circular arc section defines a plane of intersection which runs perpendicularly to a line of intersection between the first guidance surface and the first mirror plane.

9. A knee joint endoprosthesis in accordance with claim 7, wherein the line of intersection is inclined relative to a surface-normal of a tibial plane defined by the tibia component.

10. A knee joint endoprosthesis in accordance with claim 1, wherein the femur component comprises two joint surfaces which are configured to be mirror-symmetrical with respect to a second mirror plane running substantially in the anterior-posterior direction.

11. A knee joint endoprosthesis in accordance with claim 5, wherein:
the femur component comprises two joint surfaces which are configured to be mirror-symmetrical with respect to a second mirror plane running substantially in the anterior-posterior direction,
the second guidance surface is configured such that a center point is defined for each flexion angle when there is a flexion of the knee joint endoprosthesis with a flexion angle within the flexion angle range of the circular arc section, and
the center points lie on a center point plane which runs parallel to the second mirror plane but offset in a lateral direction.

12. A knee joint endoprosthesis in accordance with claim 11, wherein a spacing of the center point plane from the second mirror plane increases in dependence on the flexion angle.

13. A knee joint endoprosthesis in accordance with claim 10, wherein the two joint surfaces of the femur component comprise condyle surfaces that are arranged mirror-symmetrically with respect to the second mirror plane.

14. A knee joint endoprosthesis in accordance with claim 10, wherein:
the first guidance surface is mirror-symmetrical with respect to a first mirror plane running in the anterior-posterior direction; and
the first mirror plane and the second mirror plane are identical in an extended position of the knee joint endoprosthesis.

15. A knee joint endoprosthesis in accordance with claim 1, wherein:
the tibia component comprises a tibial part and a meniscus part that is mounted on the tibial part, and
the meniscus part comprises joint surfaces which cooperate with the joint surfaces of the femur component.

16. A knee joint endoprosthesis in accordance with claim 15, wherein the meniscus part comprises the first guide element.

17. A knee joint endoprosthesis in accordance with claim 15, wherein at least one of the meniscus part and the tibial part are configured to be mirror-symmetrical with respect to a first mirror plane running in an anterior-posterior direction.

18. A knee joint endoprosthesis in accordance with claim 10, wherein:
the first guidance surface is mirror-symmetrical with respect to a first mirror plane running in the anterior-posterior direction; and
the second mirror plane and the first mirror plane are identical for flexion angles between the tibia component and the femur component which are smaller than a limiting angle.

19. A knee joint endoprosthesis in accordance with claim 1, wherein the first radius of curvature has a value which lies in a range from approximately 7 mm up to approximately 15 mm.

20. A knee joint endoprosthesis in accordance with claim 1, wherein the pitch of the thread increases in dependence on a flexion angle of the knee joint endoprosthesis.

21. A knee joint endoprosthesis in accordance with claim 1, wherein the second guide element is formed in a region between the joint surfaces of the femur component.

22. A knee joint endoprosthesis in accordance with claim 1, wherein the second guide element is formed in a posterior end region of the femur component.

23. A knee joint endoprosthesis in accordance with claim 1, wherein at least one of the femur component and the tibia component is constructed in a one piece manner.

24. A knee joint endoprosthesis in accordance with claim 1, wherein:
the tibia component comprises a tibial part and a meniscus part that is mounted on the tibial part,
at least one of the tibial part and the meniscus part are constructed in a one piece manner.

* * * * *